United States Patent [19]

Chiesi et al.

[11] Patent Number: 5,096,929
[45] Date of Patent: Mar. 17, 1992

[54] 2-AMINO-1,2,3,4-TETRAHYDRONAPHTHA-LENE DERIVATIVES WITH CARDIOVASCULAR ACTIVITY, PROCESS FOR THEIR PREPARATION AND PHARMACEUTICAL COMPOSITIONS CONTAINING THEM

[75] Inventors: Paolo Chiesi; Stefano Bongrani; Maurizio Delcanale; Vittorino Servadio, all of Parma, Italy

[73] Assignee: Chiesi Farmaceutici S.p.A., Parma, Italy

[21] Appl. No.: 544,201

[22] Filed: Jun. 26, 1990

[30] Foreign Application Priority Data

Jun. 27, 1989 [IT] Italy .............................. 20996 A/89

[51] Int. Cl.$^5$ .................. A61K 31/135; C07C 215/64
[52] U.S. Cl. ..................................... 514/653; 564/364
[58] Field of Search ............... 564/364, 428; 514/653, 514/657

[56] References Cited

U.S. PATENT DOCUMENTS 3,536,712 10/1970 Keck et al. ......................... 564/364
4,011,258 3/1977 Wetterlin et al. ............... 260/479 R

FOREIGN PATENT DOCUMENTS 0273017 6/1986 European Pat. Off. .
0209275 1/1987 European Pat. Off. .
2123410 2/1984 United Kingdom .

Primary Examiner—Richard L. Raymond
Assistant Examiner—P. O'Sullivan
Attorney, Agent, or Firm—Mathews, Woodbridge & Collins

[57] ABSTRACT 5,6-Dimethoxy-2-[2-(4-hydroxyphenyl)-2-hydroxy-2-methylethyl]amino-1,2,3,4-tetrahydronaphthalene has inotropic and vasodilating activities and therefore can be used in the treatment of cardiocirculatory failure. The compound can be in the form of a single stereoisomer or as a mixture of two or more stereoisomers.

11 Claims, No Drawings

2-AMINO-1,2,3,4-TETRAHYDRONAPHTHALENE DERIVATIVES WITH CARDIOVASCULAR ACTIVITY, PROCESS FOR THEIR PREPARATION AND PHARMACEUTICAL COMPOSITIONS CONTAINING THEM

The present invention refers to the compound 2-amino-1,2,3,4-tetrahydronaphthalene having cardiovascular activity, to a process for its preparation, to pharmaceutical compositions containing the compound, and to its use.

BACKGROUND OF THE INVENTION

Cardiac insufficiency or cardio-circulatory failure is a major health problem. Classical therapy for many years has relied upon the use of cardiac glycosides and diuretics. More recently peripheral vasodilators also have been used.

Many patients do not respond, however, to these therapies and, as a consequence, pharmacological treatment of cardiac failure is still considered unsatisfactory, requiring therefore a search for new cardioactive drugs which are able to act on the main pathogenetic factors of the cardiocirculatory failure, namely a decrease of myocardial contractility and impairment in peripheral blood flow.

2-Amino tetrahydronaphthalene derivatives (alternatively named as 2-aminotetraline) exhibit interesting pharmacological properties because of their capacity of binding to the different receptors of the orthosympathetic system. The 5,6- and 6,7-dihydroxy derivatives of 2-aminotetraline contain, in particular, the dopamine moiety fixed in a semirigid structure which has in recent years given rise to considerable research effort.

A number of such 2-amino-tetrahydronaphthalenes are known. Gorczynski et al., J. Med. Chem., 1981, 24, 835–839 disclose 2-[1-(4-hydroxyphenyl)-but-3-ylamino]-6,7-dihydroxy-1,2,3,4-tetrahydronaphthalene.

EP-A-209275 and EP-A-273017 disclose 2-amino-6,7-dihydroxytetralin in derivatives.

EP-A-211721 disclose 2-aminotetralin compounds having lipolytic activity.

GB-A-2123410 discloses 2-amino-5,6-dihydroxytetralin derivatives having Beta- stimulating adrenergic activity.

Dopaminergic drugs can have different therapeutic uses. Drugs stimulating the post-synaptic dopamine receptors in the central nervous system (CNS) may be effective against Parkinson's disease. Drugs acting as agonists of dopamine autoreceptors, always in the CNS, may be used as antipsychotics.

Dopaminergic receptors, however, also are present on the peripheral sympathetic terminations so that much research effort recently has been directed to dopaminergic structures having peripheral cardiovascular activity.

There are a number of structure-activity studies of 2-aminotetraline derivatives giving rise to different hypothesis on the importance and effects of, for example, the configuration of the $C_2$ carbon, the optimal substitution on the amine, the kind and number of substituents on the aromatic ring, and changes of other parameters. From these studies, however, it is evident that 2-aminotetralines are rather heterogeneous as far as their pharmacological effects and their mechanism of action are concerned, the latter involving, both central and peripheral dopaminergic receptors and alpha and beta adrenergic receptors.

As with other classes of sympathicomimetics, even very small structural differences can result in remarkable effects on the degree and/or kind of activity, depending on various interdependent factors such as the kind and position of substituents, conformation, interactions with the receptor site, metabolic pathway.

DETAILED DESCRIPTION

It has now been found that the compound of formula:

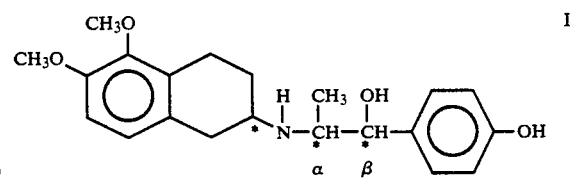

possesses with inotropic and vasodilating activities and can be advantageously used in the therapy of cardiocirculatory failure.

The compound of Formula I has three asymmetrically substituted carbon atoms (the positions of which are marked with an asterisk). It should be understood that the present invention includes all eight chiral forms—the individual stereoisomers and mixtures thereof, and the pharmaceutically acceptable salts thereof.

The compounds of the present invention can be prepared by reductive amination of 5,6-dimethoxy-2-tetralone of Formula II with the appropriate primary amine III (or the salts thereof), according to the following reaction scheme:

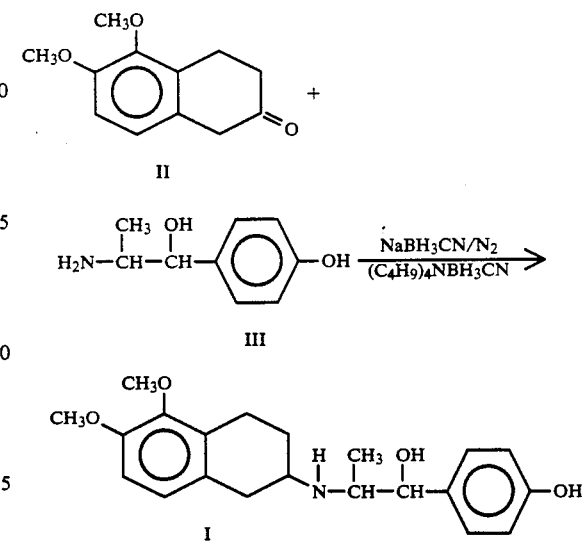

The condensation reaction is generally carried out in polar solvents such as dioxane or lower alcohols of 1 to 6 carbon atoms, preferably methanol or ethanol, at temperatures ranging from 0° C. to 40° C., preferably under an inert atmosphere, such as nitrogen. The reaction is conducted at a neutral pH adjusted by addition of an acid, such as hydrochloric or acetic acid, or of a base, such as triethylamine or pyridine.

The simultaneous reduction is effected by means of alkali hydrides, preferably sodium or lithium cyanoborohydrides or a mixture of sodium cyanoborohydride and tetrabutylammonium cyanoborohydride at a 4:1 to 1:1 weight ratio.

Alternatively, the reduction can be carried out with catalytic hydrogenation, using platinum or palladium catalysts, optionally on a carrier such as carbon. The hydrogenation can be conducted under reduced pressure or at atmospheric pressure.

The compounds are recovered from the reaction mixture by conventional methods and are generally transformed into an acid addition salt and crystallized as such.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like, preferably hydrochloric acid.

The compound of Formula I can be prepared as a single stereoisomer, or as a mixture of stereoisomers, by condensation of 5,6-dimethoxy-2-tetralone of Formula II with a p-hydroxynorephedrine stereoisomer of known configuration, optionally with subsequent separation of the epimers obtained, as for example by crystallization or by chromatography.

The intermediates used in the preparation of the compounds are known and either commercially available or readily prepared according to methods known in the literature. The stereoisomers of p-hydroxynorephedrine, for example, have been prepared by the processes described by Smith H. E. et al. in J. Med. Chem. 20(7), 978 (1977).

The Formula of compound I can also be prepared according to a different process, as shown in the following reaction scheme:

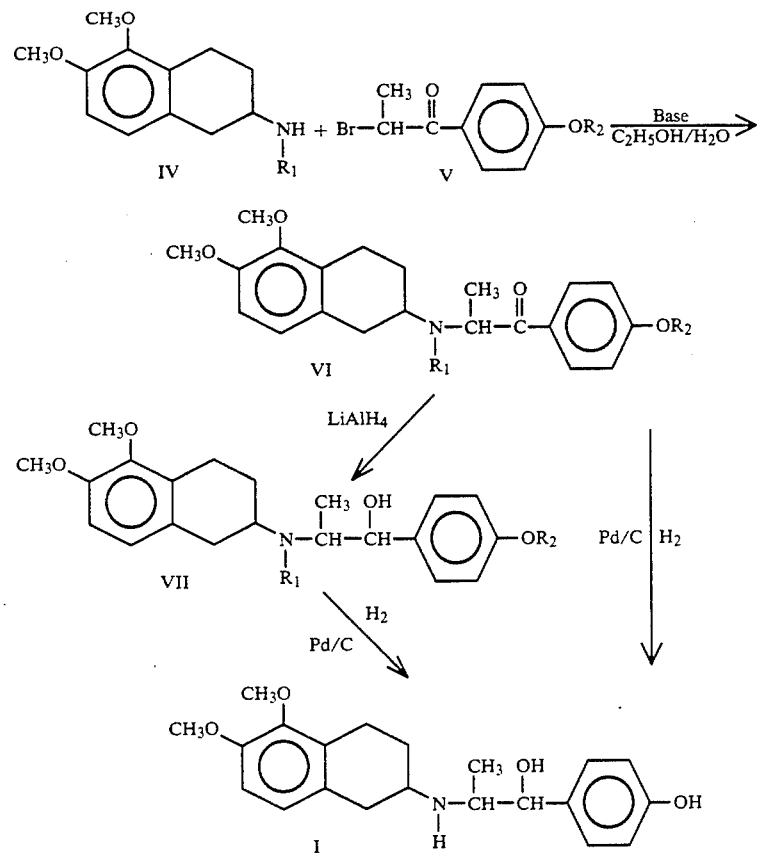

wherein $R_1$ and $R_2$ are hydrogen or a readily cleavable protecting group such as benzyl.

The condensation of the aminotetralin with the bromoketone generally is carried out in polar solvents, such as water, dioxane or lower alcohols, and preferably in ethanol or in an ethanol-water mixture, in the presence of an acid binding agent such as triethylamine or pyridine. The reaction also can be carried out in the absence of solvents at such a temperature as to allow the partial or complete melting of the reaction mixture. The subsequent reduction can be effected by hydrogenation in the presence of suited catalysts, such as platinum or palladium -on-carbon catalysts or with alkali or alkaliearth metal hydrides and subsequent hydrogenolytic debenzylation.

This process is particularly advantageous in obtaining the compounds of the invention in a given configuration. The threo-isomers, with respect to the $\alpha$ and $\beta$ carbon atoms, can be obtained, for example, by condensation of an aminotetralin (IV), in which $R_1$ is benzyl or an easily cleavable group having a similar steric hindrance, with bromoketone (V) and subsequent reduction. The presence of the benzyl group or of a group of similar steric hindrance, allows to obtain a stereospecific reduction of aminoketones (VI) so as to attain the threo form of aminoalcohols (VII), according to a modification of the process described by Van Dijk J. e Moed H. D. in Recueil 78, 22 (1959). The erythro isomers, always with respect to the α and β carbon atoms, are obtained by chemical or catalytic reduction of aminoketones (VI) wherein $R_1$=H. Compounds having a given configuration also may be obtained from the suitable aminotetraline enantiomer (IV), obtained either by enantioselective synthesis or by known separation methods. Compounds (VI) are novel and are a further object of the invention, being useful intermediates for the preparation of compounds (I).

EXAMPLE 1

(−)Erythro-5,6-Dimethoxy-2-[2-(4-hydroxyphenyl)-2-hydroxy-1methylethylamino]-1,2,3,4-tetrahydronaphthalene hydrochlormethyide (Ia).

A solution of 25 g (0.122 mole) of (±)-4-hydroxynorephedrine hydrochloride in 326 ml of methanol, adjusted to about pH 7 with 5% KOH, is slowly added to a solution containing 35.41 g (0.171 mol.) of 5,6-dimethoxy-2-tetralone in 346 ml of methanol, cooled to about 12° C. and under nitrogen atmosphere. The reaction mixture is stirred under nitrogen for about 20 hours at room temperature; thereafter a mixture of 11.84 g of $NaBH_3CN$ and 5.59 g of $(C_4H_9)_4NBH_3CN$ is added during about 2 hours, keeping the temperature below 30° C. The mixture is stirred under nitrogen for about 20 hours, then is acidified to about pH 1 with concentrated HCl and it is evaporated to dryness. The residue is taken up into 250 ml of absolute ethanol, 2,750 ml of ethyl ether are added, the obtained solid is filtered, taken up into water, adjusted to slightly basic pH (about 9.5) and extracted repeatedly with chloroform. The chloroform solutions are combined, washed with water to neutrality, dried over $Na_2SO_4$ and evaporated to dryness. The residue is taken up into 500 ml of methanol, saturated with HCl, decolorized with active charcoal, filtered, evaporated to dryness, taken up into 50 ml of absolute ethanol and precipitated with anhydrous ethyl ether. The precipitate is filtered and dried under vacuum at 40° C. 14.5 g are obtained of a mixture of the four stereoisomers (+) (αS, βR, γR); (−) (αR, βS, γS); (+) (αR, βS, γR); and (−) (αS, βR, γS). (30% yield); m.p. 202°–210° C.: MF=$C_{21}H_{27}NO_4.HCl$ MW=393.92.

Elementary analysis, IR and NMR spectra are in agreement.

EXAMPLE 2

(αS, βR)-5,6-Dimethoxy-2-[2-(4-hydroxyphenyl)-2-hydroxy-1-methylethylemino]-1,2,3,4-tetrahydronaphthalene hydrochloride (Ib).

A solution of 31.72 g (0.154 mol.) of 5,6-dimethoxy-2-tatralone in 428 ml of absolute ethanol, kept at a temperature from 10° C. to 15° C., is slowly added under nitrogen atmosphere to a solution of 13.99 g (0.084 mole) of (−) (αS, γR) 4-hydroxynorephedrine in 223 ml of absolute ethanol and glacial acetic acid to pH about 7.8. The mixture is stirred under nitrogen atmosphere for about 2 hours at room temperature. 4.51 g of 10% Pd/C are added and the mixture is hydrogenated in a Parr apparatus at room temperature at 30 p.s.i. for 20 hours. The reaction mixture is filtered, acidified to about pH 1 with HCl and evaporated to dryness. The residue is taken up into 2,000 ml of water and washed with $CHCl_3$. The aqueous phase is adjusted to pH 9.2 with 10% KOH and repeatedly extracted with CHC13. The combined organic phases are washed with water to neutrality, dried over $Na_2SO_4$, and evaporated to dryness. The residue is taken up into methanol and decolorized with activated charcoal, then filtered and evaporated under vacuum. The resulting solid is taken up in about 100 ml of absolute ethanol and the product is precipitated by addition of about 250 ml of anhydrous ethyl ether and then crystallized from 50:50 absolute ethanol/ethyl ether. 14.18 g of a mixture of the two diastereoisomers (+) (αS, βR, γS) and (+) (αS, βR, γR) are obtained (43% yield); m.p. 214–218° C. MF=$C_{21}H_{27}NO_4.HCl$ MW=393 92. [α] $c^{20}$=(C =1,87% in MeOH) −18.64.

Elementary analysis, NMR and IR spectra are in agreement.

Following the procedure described above but starting from 5,6-dimethoxy-2-tetralone and (+) (αR, S) 4-hydroxynorephedrine. (αR,βS)-5,6-dimethoxy-2-[2-(4-hydroxyphenyl)-2-hydroxy-1-methylamino]-2-hydroxy-I-methylethylamino]-!,2,3,4-tetrahydronaphthalene hydrochloride (Ic), is obtained as a mixture of the (+) (αR βS, ΓR) and (−) (αR, βS, γS) diastereoisomers, m.p. =219–221° C., MF =$C_{21}H_{27}NO_4.HCl$; MW=393.92, $[α]_D^{20}$=(C =2.002% in MeOH) −17.48.

EXAMPLE 3

Erythro-5,6-Dimethoxy-2-[2-(4-hydroxyphenyl)-2-hydroxy-1-mehylethylamino]1,2,3,4-tetrahydronaphthalene hydrochloride (Ia).

a) 5,6-dimethoxy-2-[2-(4-benzyloxyphenyl)-2-oxo-1-methylethylamino]-1,2,3,4-tetrahydronaphthalene hydrochloride.

A solution containing 20.0 g (0.082 mol.) of 5,6-dimethoxy-2-aminotetrahydronaphthalene (IV; $R_1$=H), 26.2 g (0.082 mol.) of 2-bromo-(4-benzyloxy)-1-propiophenone (V) and 9.1 g (0.09 mol.) of triethylamine in 82 ml of 95% absolute ethanol is refluxed with stirring, under nitrogen atmosphere, for 6 hours. At the end of the reaction, the solution is evaporated under vacuum, the resulting residue is taken up into 500 ml of ethyl ether, under stirring. The resulting solid is filtered, taken up into 500 ml of a 15% $K_2CO_3$ aqueous solution and extracted with ethyl acetate (3×300 ml). The organic solution is washed with water and dried over $Na_2SO_4$, then filtered and added with ether/HCl, to precipitate the product as hydrochloride, which is filtered and recrystallized from 50:50 ethanol/ether. 28.8 g of a mixture of four stereoisomers of the following configurations: (+) (αR, γR); (−) (αS, γS); (−) (αR, γS); (+) (αS, γR) are obtained (73% yield); MW 482.02; MF=$C_{28}H_{31}NO_4.HCl$ m.p. =270–275° C.

Elementary analysis and IR spectrum are in agreement.

b) Erythro-5,6-dimethoxy-2-[2-(4-hydoxyphenyl)-2-hydroxy-1-methylethylamino]-1,2,3,4-tetrahydronaphthalene hydrochloride (Ia).

Three grams of 10% Pd/C are added to a solution containing 11.0 g (0.023 mol.) of 5,6-dimethoxy-2-[2-(oxyphenyl)-2-oxo-1-methylethylamino]-1,2,3,4-tetrahydronaphthalene hydrochloride (VI; $R_1$=H, $R_2$=$CH_2C_6H_5$) in 600 ml of 95% $CH_3OH$. Hydrogenation is carried out in a Parr apparatus at room temperature and under 35 p.s.i. pressure for 30 minutes. The mixture is filtered, evaporated to dryness, and triturated thoroughly in ethyl acetate. The resulting solid is filtered, dried under vacuum and recrystallized from 50:50 ethanol/ether to obtain 5.6 g of the product (81% yield) consisting of the same stereoisomers of Example 1.

EXAMPLE 4

Threo-5,6-dimethoxy-2-[2-(4-hydroxyphenyl)-2-hydroxy-1-methylethylamino]-1,2,3,4,-tetrahydronaphthalene hydrochloride (Id).

a) 5,6-dimethoxy-2-{N-[2-(4-benzyloxyphenyl)-2-oxo-1-methylethyl]-N-benzylamino}-1,2,3,4-tetranaphthalene (VI; $R_1$, $R_2$=CH$_2$—C$_6$H$_5$).

32.1 g of 2-bromo-4-benzyloxy-1-propiophenone (V) and 14 ml of triethylamine are added to a solution of 29.7 g of 5,6-dimethoxy-2-benzylamino-1,2,3,4-tetrahydronaphthalene (IV; $R_1$=CH$_2$—C$_6$H$_5$) in 90 ml of absolute ethanol. The reaction mixture is refluxed for 8 hours, slowly adding a further 20 ml of triethylamine, and then cooled and filtered. The residue is washed with ethanol and ether. The solution is evaporated to dryness, then adjusted to pH 8.2 with methanolic potassium hydroxide, evaporated to dryness, taken up into 200 ml of chloroform, washed with water and dried over Na$_2$SO$_4$, filtered and evaporated to dryness to obtain 30 g of the product which is further purified by chromatography (eluent : 70:30 hexane/ethyl acetate) to yield 23 g of product (40% yield).

b) Threo-5,6-dimethoxy-2-{N-[2-(4-benzyloxyphenyl)-2-hydroxy-1-methylethyl]-N-benzylamino}-1,2,3,4-tetrahydronaphthalene hydrochloride (VII; $R_1$, $R_2$=CH$_2$—C$_6$H$_5$).

A solution of 3.8 g of 5,6-dimethoxy-2-{N-[2-(4-benzyl-oxyphenyl)-2-oxo-1-methylethyl]-N-benzylamino}-1,2,3,4-tetrahydronaphthalene (VI; $R_1$, $R_2$=CH$_2$—C$_6$H$_5$) in 120 ml of tetrahydrofuran are added to a suspension of 0.32 g of lithium aluminium hydride in 60 ml of tetrahydrofuran, with stirring and under nitrogen atmosphere, at a temperature below 25° C. The reaction mixture is stirred at room temperature for 30 minutes and then 1 ml of ethyl acetate is added. The mixture is stirred for 5 minutes and then filtered through Celite ®. Ether/HCl (about 20 ml) is added to the clear solution to obtain a precipitate which is filtered and dried at 50.C under reduced pressure. 3.7 g of the product are obtained (97% yield).

c) Threo-5,6-dimethoxy-2-[2-(4-hydroxyphenyl)-2-hydroxy-1-methylethylamino]-1,2,3,4-tetrahydronaphthalene hydrochloride (Ic).

2.3 g of 20% Pd/C are added to a solution containing 6.7 g di threo-5,6-dimethoxy-2-{N-[2-(4-benzyloxyphenyl)-2-naphthalene hydrochloride (VII; $R_1$, $R_2$=CH$_2$—C$_6$H$_5$) in 200 ml of absolute ethanol, then the mixture is hydrogenated in a Parr apparatus at room temperature under 35 p.s.i. pressure for 6 hours. The mixture is filtered, concentrated to about 60 ml, then ethyl ether (about 400 ml) is added thereto to complete precipitation. The resulting solid recrystallized from acetone. 3.2 g of a mixture of four stereoisomers of the following configurations: (αS, βS, γS); (αR, βR, γR); (αS, βS, γR); (αR, βR, γS); are obtained (68% yield) m.p.-200°-201° C.

Elementary analysis, IR and NMR spectra are in agreement.

EXAMPLE 5

(−) (αR, βS, γS)-5,6-dimethoxy-2-[2-(4-hydroxyphenyl)-2-hydroxy-1-methylethylamino]-1,2,3,4-tetrahydronaphthalene hydrochloride (Ie).

1.5 g of compound Ic, consisting of a mixture of the two diastereoisomers (−) (αR, βS, γS) and (+) (αR, βS, γR), are dissolved in methanol. The solvent is evaporated to give a solid foam which is taken up with 15 ml of methanol and the obtained suspension is refluxed for 4 hours. The mixture is cooled to 60° C., the solid is filtered, washed with diethyl ether and dried under vacuum at 60° C.

0.5 g of a white crystalline solid are obtained.
$[\alpha]_{589}^{20}$ = −40.27° (C=1.008 in MeOH)
$[\alpha]_{546}^{20}$ = −48.21° (C=1.008 in MeOH)
G.L.C. analysis:
% of (−) (αR, βS, γS)=93.5
% of (+) (αR, βS, γR)=6.5.

In a similar way, starting from a mixture of the two stereoisomers (+) (αS, βR, p65 R) and (−) (αS, 062 R, γS), (+) (αS, βR, γR)-5,6-dimethoxy-2-[2-(4-hydroxyphenyl)-2-hydroxy-1-methylethylamino]-1,2,3,4-tetrahydronaphthalene hydrochloride is obtained
m.p.=230°-231° C.
$[\alpha]_{589}^{20}$ = +35.85° (C=1.00 in MeOH)
$[\alpha]_{546}^{20}$ = +42.32° (C=1.00 in MeOH)
G.L.C. analysis:
% of (−) (αS, βR, γR)=92.5
% of (−) (αS, βR, γS)=7.5.

EXAMPLE 6

(+) (αR, βS, γR)-5,6-dimethoxy-2-[2-(4-hydroxyphenyl)-2-hydroxy-1-methylethylamino]-1,2,3,4-tetrahydronaphthalene hydrochloride.

a) (+) (αR,γR)-5,6-dimethoxy-2-[2-(4-benzyloxyphenyl)-2-oxo-1-methylethylamino]-1,2,3,4-tetrahydronaphthalene hydrochloride.

1.2 g of (+) (R)-5,6-dimethoxy-2-aminotetrahydronaphthalene and 1.9 g of 2-bromo-4-benzyloxy-1-propiophenone are dissolved in 11 ml of ethanol, and 0.8 of triethylamine and refluxed for 4 hours.

After standing overnight, the solid is filtered which consist of the (+) (αS, R) diastereoisomer. The filtrate is evaporated, the residue is dissolved in 5 ml of ethanol, 1.5 ml of a 10% triethylamine HCl in ethanol are added, the mixture is stirred for 1 hour and chilled at 4° C. for 2 days. The solid is filtered off, the filtrate is evaporated, the residue is dissolved in 30 ml of ethanol and, after addition of a 1 M HCl solution in methanol, the mixture is allowed to stand for 2 hours.

The precipitated solid is filtered, washed with ethanol and then with ether and dried at 40° C under vacuum.

The obtained solid is suspended in 25 ml of a refluxing 6.4 ethanol/methanol mixture for 1 hour. After standing 2 hours, the mixture is filtered, washed with diethyl ether and dried under vacuum at 40° C.

0.4 g of a white solid consisting of the stereoisomer (+) (αR, γR) are obtained with a diastereoisomeric purity of about 90%.

m p.=263°-265° C. (dec.)

By the same method, starting with (−) (S)-5,6-dimethoxy-2-aminotetrahydronaphthalene and 2-bromo-(4-benzyloxy)-1-propiophenone, there is obtained (−) (oS,S)-5,6-dimethoxy-2-[2-(4-benzyloxyphenyl)-2-oxo-1-methylamino]-1,2,3,4-tetrahydronaphthalene.
$[\alpha]_{546}^{20}$ = −49.03° (C=1.03 in MeOH)
G.L.C. analysis:
% of (−) (αS, βR, γS)=95.9
% of (−) (αR, βS, γS)=4.1.

b) (+) (αR, βS, γS)-5,6-dimethoxy-2-[2-(4-hydroxyphenyl)-2-hydroxy-1-methylethylamino]-1,2,3,4-tetrahydronaphthalene hydrochloride.

0.4 g of (+) (αR, γR)-5,6-dimethoxy-2-[2-(4-benzyloxyphenyl)-2-oxo-1-methylethylamino]-1,2,3,4-tetrahydronaphthalene hydrochloride are suspended in 25 ml of methanol. 0.1 g of 5% Pd/C are added and the mixture is hydrogenated at 35 p.s.i. under stirring.

The catalyst is filtered, the solvent is evaporated and the solid foam is dissolved in 10 ml of warm acetone, filtering off the solid residue, cooled to room temperature under stirring. After standing overnight, the solid is filtered, washed with diethyl ether and dried at 70° C. under vacuum for 24 hours.

0.2 g of (+) (αR, βS, γR) isomer are obtained
$[\alpha]_{589}^{20} = +51.45°$ (C=1.036 in MeOH)

isoproterenol which was determined at the beginning of the test. In Table 1 the potency (EC50=effective concentration inducing the 50% of the maximal effect) and the relative intrinsic activity (expressed as α and compared with that of isoproterenol, taken=1) are shown.

In addition to compound Ia, three other 2-aminotetralin derivatives, compound 14 (reported by Gorczynski R. J. et al. in J. Med. Chem. 1981., 24, 835–839), compound (VIII), and compound (IX), were assayed in this test.

For the sake of brevity, the compounds will be identified hereinafter by means of the experimental abbreviations (CHF#).

TABLE I

Potency (EC$_{50}$) and intrinsic activity (α) of 2-aminotetralin derivatives in the isolated rat left atrium and right atrium, compared with dopamine (confidence limits shown in parentheses).

| Compound | R$_1$, R$_2$ | R | Left atrium (force) EC$_{50}$ (H) | α | Right atrium (frequency) EC$_{50}$ (H) | α |
|---|---|---|---|---|---|---|
| dopamine | — | | 1.2 × 10$^{-6}$ (1.0–3.1) | 0.95 (0.90–1.0) | 1.9 × 10$^{-6}$ (1.5–2.4) | 1.06 (0.87–1.24) |
| Ia (CHF 1255) | OCH$_3$– | –CH(CH$_3$)CH(OH)–C$_6$H$_4$–OH | 3.0 × 10$^{-6}$ (2.3–3.9) | 0.60 (0.52–0.68) | 1.3 × 10$^{-6}$ (0.9–2.0) | 0.55 (0.46–0.64) |
| Control Compound (CHF 1026) | OH– | –CH(CH$_3$)CH$_2$CH$_2$–C$_6$H$_4$–OH | 0.9 × 10$^{-6}$ (0.6 × 10$^{-6}$–1.2 × 10$^{-7}$) | 0.81 (0.73–0.89) | 1.3 × 10$^{-7}$ (8.5 × 10$^{-8}$–2.1 × 10$^{-7}$) | 0.86 (0.72–0.99) |
| VIII (CHF 1296) | OCH$_3$– | –CH$_2$CH(OH)–C$_6$H$_4$–OH | Inactive | | | |
| IX (CHF 1297) | OCH$_3$– | –CH$_2$CH(OH)–C$_6$H$_4$(OH) | Inactive | | | |

$[\alpha]_{546}^{20} = +60.91°$ (C=1.036 in MeOH)
G.L.C. analysis:
% of (+) (αR, βS, γR)=98.49
% of (−) (αS, βR, γR)=1.51.

The inotropic and chronotropic effects of compound (Ia) of the invention were determined in vitro using, respectively, isolated rat left atrium and right atrium.
Left atrium:inotrocic activity The atria were subjected to a 0.5 g starting tension and suspended in a bath containing aerated Krebs-Henseleit j solution with 95% O$_2$ and 55° CO$_2$ kept at 32.C. The preparation was stimulated at a 4 Hz frequency with pulses during 5 msec each. The contraction strength was detected by an isometric transducer and recorded on a microndynamometer.
Right atrium:chronotrpic activity The preparation was prepared in the same way and under the same conditions as described above, but was not subjected to electric stimulation. Frequency was monitored by a cardiotachograph.

The results were expressed as the percentage of the response obtained with a maximal dose (10$^{-8}$ M) of As it oan be seen from the data reported in Table 1, CHF 1255 exerted a cardiostimulating activity with a potency comparable to those of dopamine and of CHF 1026.

Contrary to the control compounds, however, CHF 1255 showed a reduced intrinsic activity : therefore, based on it activity, which, as will be evidenced hereinafter, the compound exhibits beta-1 stimulution, it being a partial agonist of beta-1 adrenergic receptors. This behavior was further confirmed in the isolated left atria of other animal species (cat and guinea pig), in which the compound shows an inotropic activity with an effectiveness of 45–31% that of isoproterenol. The partial agonism of CHF 1255 towards beta-1 adrenergic receptors is of great importance for the characterization of the compound.

In fact, the research efforts have been directed for some time to the synthesis and development of partial agonistic beta-1 stimulating molecules. Based on this assumption, prenalterol and, more recently, xamoterol, have been prepared, the latter being less effective an agonistic action 40% that of isoproterenol) but better tolerated.

The rational of the therapy with partial agonists is related to the induction of a beta-agonistic effect that can be modulated. As a matter of fact these compounds, acting both as agonists and as antagonists, stimulate the impaired cardiac function in patients affected with cardiac failure, under rest or reduced exercise conditions. During physical exercise, on the other hand, when the sympathetic tonus is high, they are able to protect the heart against adrenergic overstimulation, antagonizing its effects.

Another important fact evident from Table 1 is that CHF 1296 and CHF 1297 proved to be completely inactive, further confirming thereby that minimal structural changes play in this kind of compounds fundamental role for the activity.

The mechanism of the inotropic activity of CHF 1255 has been studied in a series of other tests.

It has been possible to show, as previously said, that this activity is due to the stimulation of beta-1 adrenergic receptors. Studies have excluded the possibility that the cardiostimulant action of the compound is due to catecholamines release, to the stimulation of alpha-adrenergic cardiac receptors, or to the stimulation of histaminergic $H_1$ and $H_2$ receptors. The cardiostimulant activity of CHF 1255 also is not due to phosphodiesterase inhibition.

Isolated rat left atrium: interactions with beta-adrenercic receptors.

The affinity for beta-1 adrenergic receptors has been evaluated in the rat left atrium as previously described.

In this test, dose-response curves of CHF 1255 were recorded in the absence and in the presence of increasing concentrations ($10^{-8}$ to $3 \times 10^{-7}$ M) of the selective beta-1 blocker atenolol.

The pre-treatment with the beta-1 blocker shifted the dose-responsive curve of CHF 1255 to the right in a dose-dependent way, showing therefore for this compound an interaction of competitive type for the beta-1 adrenergic receptors.

The selectivity of this interaction has been studied by evaluating the effects on beta-2 adrenergic receptors, in the guinea-pig isolated trachea, using CHF 1026 as reference compound.

Isolated guinea-pig trachea: interactions with beta-2 adrenergic receptors

Trachea strips were isolated and prepared according to the method described by Emerson J and Machay D in J Pharm Pharmacol 1979, 31, 798, immersed in Krebs-Henseleit solution (37° C., 95% $O_2$+5% $CO_2$), subjected to an initial tension of 1 g and contracted with carbachol ($3 \times 10^{-7}$ M).

Dose-response curves of CHF 1255 and CHF 1026 were recorded in the absence and in the presence of $10^{-6}$ M propranolol, used as antagonist and added to the bath before the stimulation with carbachol.

The obtained results are shown in Table 2, expressed as potency ($EC_{50}$ calculated from t he dose—response curve) and intrinsic activity ($\alpha$, isoproternol=1).

TABLE 2

Potency ($EC_{50}$) and intrinsic activity ($\alpha$) of CHF 1255 and CHF 1026 in the isolated guinea-pig trachea.

| Compounds | in absence of propanolol | | in presence of propanolol | |
|---|---|---|---|---|
| | $EC_{50}$ (M) | α | $EC_{50}$ (M) | α |
| Ia | $3.4 \times 10^{-6}$ | 0.94 | $4.6 \times 10^{-6}$ | 0.72 |

TABLE 2-continued

Potency ($EC_{50}$) and intrinsic activity ($\alpha$) of CHF 1255 and CHF 1026 in the isolated guinea-pig trachea.

| Compounds | in absence of propanolol | | in presence of propanolol | |
|---|---|---|---|---|
| | $EC_{50}$ (M) | α | $EC_{50}$ (M) | α |
| (CHF 1255) | (2.8–4.1) | (0.90–0.98) | (3.3–6.5) | (0.62–0.83) |
| Ref. Compound (CHF 1026) | $2.3 \times 10^{-7}$ (1.6–3.2) | 0.99 (0.99–1.00) | $1.3 \times 10^{-4}$ (0.8–1.9) | 0.94 (0.82–1.06) |

Both compounds exert a dose-dependent inhibition of the carbachol-induced contractions. In the presence of propranolol the dose-response curve of CHF 1026 is parallelely shifted to the right, showing a competitive antagonistic action. The effects of CHF 1255 remain unchanged.

According to these results, it is possible to state that in contrast to CHF 1026,° C.HF 1255 does not stimulate beta-2 adrenergic receptors. The relaxing effect is probably to be ascribed to other mechanisms, since it is not competitively antagonized by a high dose of propranolol.

Because of its selective agonistic activity on adrenergic beta-1 receptors, CHF 1255, unlike CHF 1026, has no tachycardic and arrhythmogenic activity due to the stimulation of beta-2 receptors.

The activity of CHF 1255 also has been compared with two recently introduced inotropic drugs, having different mechanisms of action, xamoterol fumarate and amrinone, the former being a partial agonist of adrenergic beta-1 receptors and the latter being an inhibitor of phosphodiesterase.

Comparison of inotroic activity of CHF 1255 with xamoterol and amrinone.

The effects of the compounds were evaluated in rat isolated atria according to the previously described method. The results are reported in Table 3.

Table 3. Potency (EC50) and intrinsic activity (α;isoproterenol=1) on the isolated rat left atrium (Inotropic activity) and right atrium (chronotropic activity).

| Com-pounds | Left atrium (force) | | Right atrium (frequency) | |
|---|---|---|---|---|
| | $EC_{50}$ (M) | α | $EC_{50}$ (M) | α |
| Dop-amine | $1.19 \times 10^{-6}$ (1.05–1.35) | 0.95 (0.90–1.0) | $1.89 \times 10^{-6}$ (1.47–2.45) | 1.06 (0.87–1.24) |
| CHF 1255 | $3.01 \times 10^{-6}$ (2.35–3.87) | 0.60 (0.52–0.68) | $1.32 \times 10^{-6}$ (0.88–1.97) | 1.60 (0.56–0.65) |
| Am-rinone | $2.66 \times 10^{-5}$ (1.05–6.74) | 0.29 (0.20–0.37) | $1.55 \times 10^{-4}$ (0.54–4.45) | 1.47 (0.41–0.54) |
| Xam-oterol | $4.98 \times 10^{-9}$ (3.90–6.37) | 0.33 (0.28–0.38) | $4.71 \times 10^{-9}$ (3.48–6.37) | 0.76 (0.66–0.86) |

The potency of CHF 1255, expressed as contraction producting 50% of the maximum effect (increase of contraction force), is about 10 times higher than that of amrinone and about 300 times lower than that of xamoterol.

It should be noticed that the chronotropic efficacy of CHF 1255 is remarkably lower than that of xamoterol. This is very important because an inotropic drug should not cause an excessive increase of heart-rate.

CHF 1255 also induces an important hemodynamic action, differently from xamoterol Rat perfused hind quarter; vasodilating action The vasodilating effect of CHF 1255 has been evaluated in the arterial rat hind quarter perfused with Krebs-Henseleit solution at constant flow.

The increase of arterial resistance was induced by $K^+$—enriched solution (40 mM), norepinephrine ($5\times 10^{-6}$ M) and serotonin ($5\times 10^{-7}$ M).

Papaverine and prazosin, powerful α-blocker vasodilator, were used as reference compounds.

The results are reported in Table 4.

Table 4. POtency ($ED_{40}$) and efficacy ($\alpha$) of the tested compounds in reducing the arterial resistance induced in rat hind quarter by different agents.

$ED_{40}$=dose (moles) decreasing of 40% the contraction induced by the agonist. 100% was considered as the complete recduction of contraction.

| Compounds | K+ ($ED_{40}$) | α | Nore-Pine Phrine ($ED_{40}$) | α | 5-HT ($ED_{40}$) | α |
|---|---|---|---|---|---|---|
| CHF 1255 | $1.5 \times 10^{-6}$ | 46 | $1.2 \times 10^{-8}$ | 94 | $6.5 \times 10^{-7}$ | 60 |
| PAPA-VERINE | $6.5 \times 10^{-8}$ | 90 | $4.5 \times 10^{-8}$ | 95 | $5.0 \times 10^{-8}$ | 90 |
| PRAZ-OSIN | inactive | | $1.5 \times 10^{-11}$ | 96 | inactive | |

CHF 1255 is active against the different agents but, differently from papaverine having the same $ED_{40}$ for the different experimental conditions, proved to be particularly active on the norepinephrine induced contraction.

This effect is due to an α-blocking activity whereas the activity against the potassium or serotonin induced contraction is probably due to an aspecific mechanism which could even account for the relaxing activity on the isolated guinea-pig trachea which is not mediated by beta-2 receptors.

The α-blocking activity of CHF 1255 has been confirmed in the rabbit isolated aorta, with a competitive inhibition of the noprepinephrine dose—response curve.

The interesting hemodynamic properties of CHF 1255 were confirmed in vivo in the anesthetized dog.
Anesthesized dog: cardiovascular activity Beagle dogs were anesthetized with sodium pentobarbital (30 mg/kg iv) thoracotomized and monitored by recording cardiocirculatory parameters.

CHF 1255 and the reference drugs (amrinone and xamoterol) were administered i.v. in a bolus.

CHF 1255 at the doses of 0.3—1.3 μmoles/kg i.v. confirmed its activity in changing hemodynamic parameters.

It has in fact, and in contrast to xamoterol whose effects are negligible, a good hypotensive action (respectively −17, −22 and −31%) and a marked reduction of the systemic arterial resistances (−28, −37 and −45%), together with a significant increase of the stroke volume (10, 16 and 21) and of the cardiac output (17, 28 and 34%).

It should be noted that the hemodynamic effects are more relevant than those of amrinone (1-3-10 μmol/kg iv).

CHF 1255 showed also remarkable inotropic effect increasing the dF/dT index (peak of the first derivative of the aortic flow in ml/seconds-2) useful for the evaluation of the cardiac function.

CHF 1255 has shown, therefore, to have a very interesting pharmacological profile and it has to be considered as belonging to the class of "inodilators" since it is endowed with both inotropic and vasodilator actions.

Its activity is also long-lasting, probably because it is not easily subjected to metabolic inactivation by catechol-0-methyltransferases (COMT), as a result of the methylation of the catechol groups.

We have also studied whether the pharmacodynamic effects of CHF 1255 were to be acribed to a particular isomer, by carrying out tests using the diastereoisomeric mixture (αS, βR) (CHF 1389) and the diastereoiisomeric mixture (αR, βS) (CHF 1388).

CHF 1389 proved to be as effective as CHF 1255 in the rat isolated left atrium whereas CHF 1388 did not show any inotropic activity.

On the other hand, the vasodilating activity of CHF 1255 is mainly due to CHF 1388.

The overall activity of CHF 1255 (Compound Ia) is therefore due to an interaction of the effects produced by the two diastereoisomeric mixtures, each having its specific action so as to justify an independent therapeutic use.

Evaluation of acute toxicities

The results are shown in Table 5.

| Animal | Sex | Administration route | Acute Toxicity mean LD$_{50}$ mg/kg |
|---|---|---|---|
| mouse | male | os | 325 (286–364) |
| rat | male/female | os | 1269 (762–2144) |
| mouse | male | i.v. | 65 (55–78) |
| rat | male/female | i.v. | 59 (55–64) |

The present invention also relates to pharmaceutical compositions containing as the active ingredient the compound of Formula I or one of the isomerss thereof as such or ifn the form of a pharmaceutically acceptable salt thereof, in combination with pharmaceutically acceptable excipients. These compositions can be ussed for the cardiovascular therapy, particularlfy as inotropic agents.

The compositions preferably will be administered the oral or parenteral routes, in form of. capsuless, tablets or vials respectively.

Pharmaceutical compositions for the oral administration, preferably in unit dosess, can be prepared by admixing the active ingredient with a solid powdered excipient, such as lactose, saccharose, sorbitol, manitol; potato, cereal or maize starch, amylopectin, cellulose or gelatin derivatives, and optionally also with lubricants such as talc, magnesium or calcium stearate, polyethylene glycol or silica.

Tablets can be coated according to well-known pharmaceutical techniques. Hard gelatin capsules can contain granulates of the active ingredient, together with solid powdered excipientss, such as lactose, saccharose, sorbitol, mannitol, starches of the above indicated types, cellulose or gelatin derivatives, and they can also containf stearic acid or magnesium stearate or talc. The unit dose for oral formulations will range from about 10 to about 100 mg of the active ingredient.

In case of injectable formulations for the parenteral administration, the excipients can be a pharmaceutically acceptable sterile liquid, such as water or an aqueous polyvinylpyrrolidone solution and optionally a stabilizer and/or a buffer.

The active ingredient can be dissolved in the liquid and filter sterilized before the distribution into vials, or it can be directly freeze-dried, in which case vials containing injection liquid will be contained in the packagess, to restore the solution before use.

Another particularly advantageous for administration of the compounds of the invention is transdermal. Systems which consist of an adhesive matrice thus can be applied to the skin with the active ingredient incorporated in an appropriate concentration and gradually released through the skin to enter the bloodstream.

What is claimed is:

1. A compound selected from the group consisting of (i) a stereoisomer or mixture of stereoisomers of the formula:

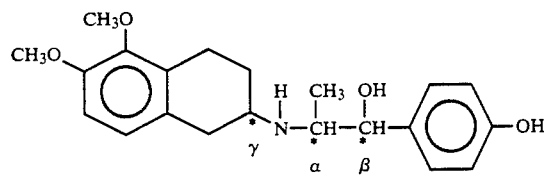

and (ii) the pharmaceutically acceptably salts of said stereoisomer or mixture of stereoisomers.

2. A compound according to claim 1 which is erythro5,6-dimethoxy2-[2-(4-hyroxyphenyl)-2-hyroxy-10methylethylamino]-1,2,3,4-tetrahydronaphthalene or a pharmaceutically acceptable salt thereof.

3. A compound according to claim 1 in which threo-5,6-dimethoxy-2-[2-(4-hyroxyphenyl)-2-hydroxy-1-methylethylamino]-1,2,3,4-tetrahydronaphthalene or a pharmaceutically acceptable salt thereof.

4. A compound according to claim 1 wherein the configuration about the carbon atom designated $\alpha$ is R and the configuration about the carbon atom designated $\beta$ is S.

5. A compound according to claim 4 which is $(-)(\alpha R, \beta S, \gamma S)$-5,6-dimethoxy-2-(4-hyroxyphenyl)-2-hydroxy-1methylethylamino]-1,2,3,4-tetrahydronaphthalene or a pharmaceutically acceptable salt thereof.

6. a compound according to claim 4 which is $(+)(\alpha R, \beta S, \gamma R)$-5,6-dimethoxy-2-[2-(4-hydroxyphenyl)-2-hydroxy-1methylethylamino]-1,2,3,4-tetrahydronaphthalene or a pharmaceutically acceptable salt thereof.

7. A compound according to claim 1 wherein the configuration about the carbon atom designated $\alpha$ is S and the configuration about the carbon atom designated $\beta$ is R.

8. A compound according to claim 7 which is $(+)(\alpha S, \beta R, \gamma R)$-5,6-dimethoxy-2-[2-(4-hydroxyphenyl)-2-hyroxy-1-methylethylamino]-1,2,3,4-tetrahydronaphthalene or a pharmaceutically acceptable salt thereof.

9. A compound according to claim 7 which his $(-)(\alpha S, \beta R, \gamma S)$-5,6-dimethoxy-2-[2-(4-hydroxyphenyl)-2-hydroxy-1-methylethylamino]-1,2,3,4-tetrahydronaphthalene or a pharmaceutically acceptable salt thereof.

10. A pharmaceutical composition comprising a quantity of a compound according to claim 1 sufficient to effect stimulation of cardiac $\beta_1$ adrenergic receptors, and a pharmaceutical carrier.

11. The method of stimulation of cardiac $\beta_1$ adrenergic receptors in a human in need thereof which comprises administering thereto an effective amount of a compound according to claim 1.

* * * * *